US00PP16409P2

(12) United States Plant Patent
Sugii

(10) Patent No.: US PP16,409 P2
(45) Date of Patent: Apr. 4, 2006

(54) ***PETUNIA* PLANT NAMED 'USUZUMI'**

(50) Latin Name: *Petunia×hybrida*
Varietal Denomination: Usuzumi

(75) Inventor: Akemi Sugii, Chiba (JP)

(73) Assignee: Suntory Flowers Limited, Tokyo (JP)

( * ) Notice: Subject to any disclaimer, the term of this patent is extended or adjusted under 35 U.S.C. 154(b) by 84 days.

(21) Appl. No.: 11/036,784

(22) Filed: Jan. 14, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L. Bell
(74) *Attorney, Agent, or Firm*—C. A. Whealy

(57) ABSTRACT

A new and distinct cultivar of *Petunia* plant named 'Usuzumi', characterized by its upright and outwardly spreading plant habit; vigorous growth habit; numerous light purple-colored flowers with dark purple-colored venation and throats; long flowering period; and good garden performance.

1 Drawing Sheet

Botanical designation: *Petunia×hybrida.*
Cultivar denomination: 'Usuzumi'.

BACKGROUND OF THE INVENTION

The present Invention relates to a new and distinct cultivar of *Petunia* plant, botanically known as *Petunia×hybrida*, and hereinafter referred to by the cultivar name Usuzumi.

The new *Petunia* is a product of a planned breeding program conducted by the Inventor in Abo-gun, Chiba, Japan. The objective of the breeding program is to create new *Petunias* with numerous flowers with attractive flower colors.

The new *Petunia* originated from a cross-pollination made by the Inventor in July, 2000 of an unnamed proprietary *Petunia* selection, not patented, as the female, or seed parent, with an unnamed proprietary *Petunia* selection, not patented, as the male, or pollen parent. The new *Petunia* was selected as a single plant from the resulting progeny of the cross-pollination by the Inventor in a controlled environment in Abo-gun, Chiba, Japan.

Asexual reproduction of the new cultivar by terminal cuttings in a controlled environment in Abo-gun, Chiba, Japan since September, 2002 has shown that the unique features of this new *Petunia* are stable and reproduced true to type in successive generations.

SUMMARY OF THE INVENTION

Plants of the cultivar Usuzumi have not been observed under all possible environmental conditions. The phenotype may vary somewhat with variations in environment such as temperature and light intensity without, however, any variance in genotype.

The following traits have been repeatedly observed and are determined to be the unique characteristics of 'Usuzumi'. These characteristics in combination distinguish 'Usuzumi' as a new and distinct *Petunia* cultivar:

1. Upright and outwardly spreading plant habit.
2. Vigorous growth habit.

3. Numerous light purple-colored flowers with dark purple-colored venation and throats.
4. Long flowering period.
5. Good garden performance.

Plants of the new *Petunia* differ primarily from plants of the female parent selection in the following characteristics:

1. Plants of the new *Petunia* are taller than plants of the female parent selection.
2. Plants of the new *Petunia* have elliptic-shaped leaves whereas plants of the female parent selection have oval-shaped leaves.
3. Plants of the new *Petunia* and the female parent selection differ in flower coloration.

Plants of the new *Petunia* differ primarily from plants of the male parent selection in the following characteristics:

1. Plants of the new *Petunia* are taller than plants of the male parent selection.
2. Growth habit of plants of the new *Petunia* is upright and outwardly spreading whereas growth habit of plants of the male parent is decumbent.
3. Plants of the new *Petunia* have larger flowers than plants of the male parent selection.
4. Plants of the new *Petunia* and the male parent selection differ in flower coloration.

Plants of the new *Petunia* can be compared to plants of the cultivar Revolution Bluevein, disclosed in U.S. Plant Pat. No. 9,322. In side-by-side comparisons conducted in Abo-gun, Chiba, Japan, plants of the new *Petunia* differed from plants of the cultivar Revolution Bluevein in the following characteristics:

1. Plants of the new *Petunia* were taller than plants of the cultivar Revolution Bluevein.
2. Growth habit of plants of the new *Petunia* was upright and outwardly spreading whereas growth habit of plants of the cultivar Revolution Bluevein was decumbent.
3. Plants of the new *Petunia* had thicker stems than plants of the cultivar Revolution Bluevein.
4. Plants of the new *Petunia* had elliptically-shaped viscid leaves whereas plants of the cultivar Revolution Bluevein had oval-shaped smooth leaves.

5. Plants of the new *Petunia* and the cultivar Revolution Bluevein differed in flower coloration.
6. Plants of the new *Petunia* flowered longer than plants of the cultivar Revolution Bluevein.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Usuzumi' grown in a container.

The photograph at the bottom of the sheet comprises a close-up view of typical flowers of 'Usuzumi'.

DETAILED BOTANICAL DESCRIPTION

The aforementioned photographs and following observations and measurements describe plants grown in Abo-gun, Chiba, Japan, in a polyethylene-covered greenhouse during the late spring with day temperatures about 28° C. and night temperatures about 18° C. Plants were grown for five months in 15-cm containers. Plants were pinched one time in the spring. Color references are made to The Royal Horticultural Society Colour Chart, 2001 Edition, except where general terms of ordinary dictionary significance are used.

Botanical classification: *Petunia×hybrida* cultivar Usuzumi.

Parentage:

*Female parent.*—Unnamed proprietary *Petunia* selection, not patented.

*Male parent.*—Unnamed proprietary *Petunia* selection, not patented.

Propagation:

*Type cutting.*—Terminal vegetative cuttings.

*Time to initiate roots.*—About one week at 18° C.

*Time to develop roots.*—About two weeks at 18° C.

*Root description.*—Fine, fibrous, white in color.

*Rooting habit.*—Freely branching, dense.

Plant description:

*Form.*—Annual flowering plant; indeterminate; upright and outwardly spreading plant habit. Viscid and glandular pubescent. Vigorous growth habit.

*Branching habit.*—Freely branching with lateral branches developing potentially at every node.

*Plant height.*—About 50 cm.

*Plant diameter.*—About 40 cm.

*Lateral branches.*—Length: About 20 cm. Diameter: About 3 mm. Internode length: About 3 cm. Texture: Pubescent. Color: 144B.

*Foliage description.*—Arrangement: Alternate, simple; sessile. Length: About 6.5 cm. Width: About 3.5 cm. Shape: Elliptic. Apex: Acute. Base: Cuneate. Margin: Entire. Texture, upper and lower surfaces: Pubescent; viscid. Venation pattern: Pinnate; reticulate. Color: Developing and fully expanded foliage, upper surface: 137A. Developing and fully expanded foliage, lower surface: 137B. Venation, upper and lower surfaces: Similar to lamina.

Flower description:

*Flower type and habit.*—Single salverform flowers; flowers face mostly upward or outward; axillary. Flowers not persistent. Freely flowering habit.

*Natural flowering season.*—Plants flower from April through late November in Japan; flowering continuous during this period.

*Flower longevity on the plant.*—About three to four days.

*Fragrance.*—None detected.

*Flower size.*—Diameter: About 5 cm. Depth: About 4 cm.

*Flower buds.*—Length: About 3.7 cm. Diameter: About 7 mm. Shape: Cylindrical. Color: 79D.

*Corolla.*—Quantity/arrangement: Five petals; fused, funnelform. Petal length from throat: About 1.5 cm. Petal width: About 2.3 cm. Petal shape: Roughly spatulate or fan-shaped. Petal apex: Cuspidate. Petal margin: Entire. Petal texture: Smooth; satiny. Color: Petal, upper surface, when developing and fully expanded: 76D; venation, 86A. Petal, lower surface, when developing and fully expanded: 76D; venation, 83A; color becoming closer to 76C with development. Flower throat (inside): 86A. Flower tube (outside): 86A.

*Sepals.*—Arrangement/appearance: Single whorl of five sepals fused at base, star-shaped. Length: About 1 cm. Width: About 1.5 mm. Shape: Oblong. Apex: Obtuse. Margin: Entire. Texture, upper and lower surfaces: Pubescent. Color, upper and lower surfaces: 137B.

*Peduncles.*—Length: About 2 cm. Width: About 1.5 mm. Angle: About 45° from the stem. Strength: Moderately strong. Texture: Pubescent. Color: 144B.

*Reproductive organs.*—Stamens: Quantity: Five per flower. Anther shape: Ellipsoidal. Anther length: About 1.5 mm. Anther color: 94D. Pollen amount: Moderate. Pollen color: 94D. Pistils: Quantity: One per flower. Pistil length: About 2 cm. Style length. About 1.9 cm. Style color: 144D. Stigma shape: Broadly elliptic. Stigma color: 79A. Ovary color: 141B.

*Seed.*—Diameter: About 0.5 mm. Color: Brownish.

Disease/pest resistance: Plants of the new *Petunia* have not been noted to be resistant to specific pathogens and pests common to *Petunia.*

Garden performance: Plants of the new *Petunia* have been observed to have good garden performance and tolerate rain, wind and tolerated temperatures from −5 to 35° C.

It is claimed:

1. A new and distinct cultivar of *Petunia* plant named 'Usuzumi', as illustrated and described.

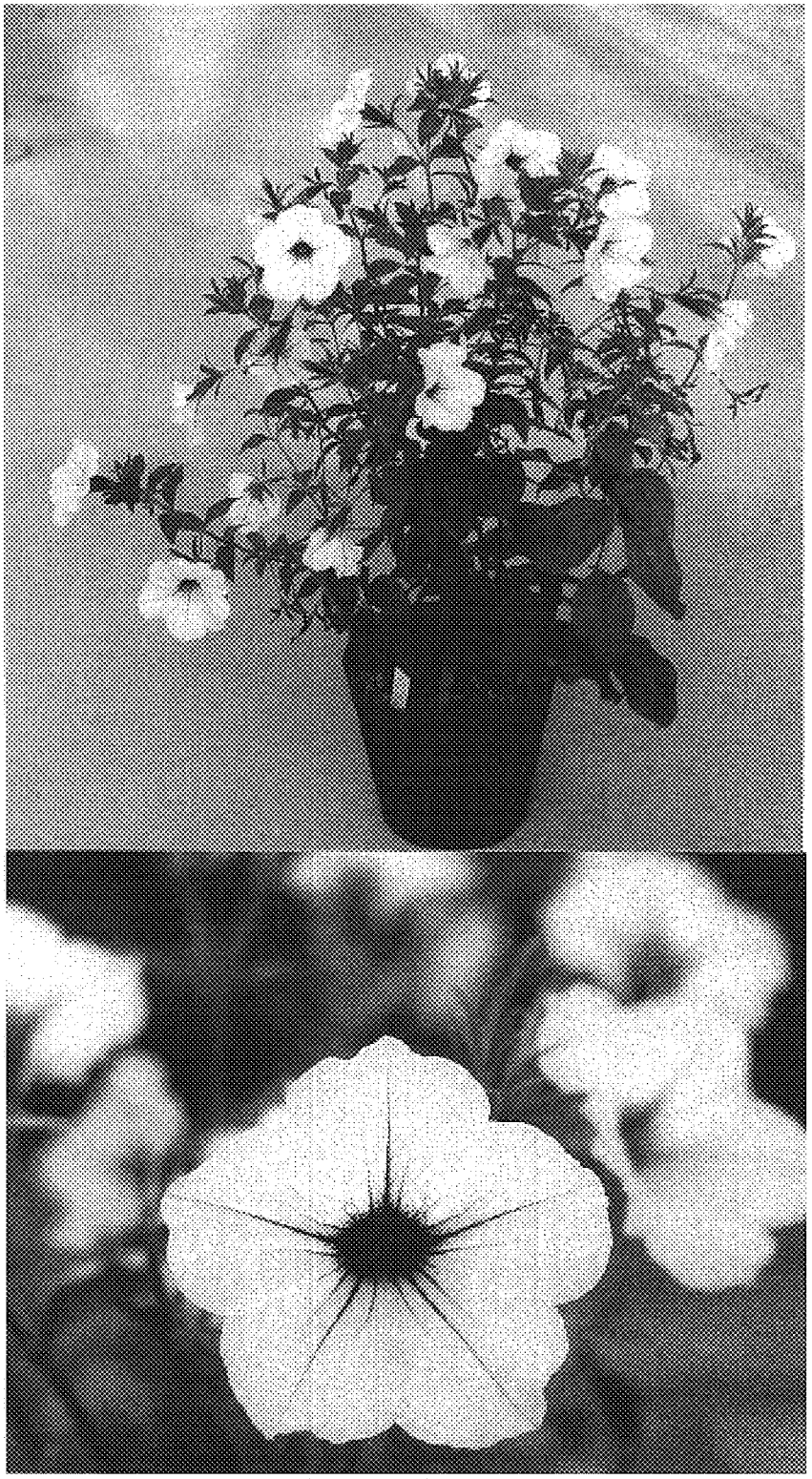

* * * * *